Patent Number: 5,352,693
Date of Patent: Oct. 4, 1994

United States Patent [19]
Farina

[54] PRESERVATIVE MIXTURES
[75] Inventor: Thomas E. Farina, Flemington, N.J.
[73] Assignee: Lonza Inc., Fair Lawn, N.J.
[21] Appl. No.: 951,573
[22] Filed: Sep. 25, 1992
[51] Int. Cl.[5] .................. A61K 31/235; A61K 31/415
[52] U.S. Cl. .................................... 514/398; 514/532; 514/544
[58] Field of Search ................ 514/847, 398, 532, 544

[56] References Cited

U.S. PATENT DOCUMENTS 4,496,576  1/1985  Loncrini et al.
4,908,456  3/1990  Farina et al. .......................... 548/312
5,037,843  8/1991  Schoenberg .......................... 514/389

OTHER PUBLICATIONS

D. N. Maddox, "The Role of p-Hydroxybenzoates in Modern Cosmetics," *Cosmetics & Toiletries*, vol. 97 (Nov., 1982), pp. 85–88.

Joel E. Rogelberg, "Dantogard: A New EPA Registered Preservative," *HAPPI*, Mar., 1986, pp. 60, 63–64.

Marvin Rosen, "A New Preservative," *Soap/Cosmetics/Chemical Specialties*, Mar., 1986, pp. 28–29, 78.

*Primary Examiner*—Marianne M. Cintins
*Assistant Examiner*—Phyllis G. Spivack
*Attorney, Agent, or Firm*—Darby & Darby

[57]  ABSTRACT

A solid composition comprising a dispersion of at least one alkyl ester of p-hydroxybenzoic acid in a hydroxymethyl-substituted dimethylhydantoin, its method of preparation, and its use as a preservative in shampoos, lotions, and cosmetics.

9 Claims, No Drawings

PRESERVATIVE MIXTURES

BACKGROUND OF THE INVENTION

The need for preservatives in the cosmetic and allied industries has long been recognized. Among those most commercially acceptable are the esters of p-hydroxybenzoic acid (parabens) and substituted dimethylhydantoin-based products. Their use individually is described by D. N. Maddox, "The Role of p-Hydroxybenzoates in Modern Cosmetics" (*Cosmetics & Toiletries*, Vol 97 Nov 1982 pp 85–88), Joel E Rogelberg "Dantogard: A New EPA Registered Preservative" (*HAPPI*, March 1986, pp. 60, 63–64), and M. Rosen, "A New Preservative: EPA Registered 'Dantogard' Protects Water-Based Household, I&I Products from Microbial Contamination" (*Soap/Cosmetics/Chemical Specialties*, March 1986, pp. 28–29, 78). To broaden the spectrum of the microbial activities, these two classes of materials have been formulated together in a variety of different proportions (U.S. Pat. No. 4,496,576).

The availability of a solid form of 1,3-bis(hydroxymethyl)-5,5-dimethylhydantoin (DMDMH), its method of preparation, and its melt properties allow the preparation of virtually all combinations of parabens, at levels not possible with the commercial aqueous solutions of DMDMH. Unfortunately, the parabens have low water solubility and combinations with aqueous DMDMH solutions, for the purpose of providing broad spectrum preservatives, require large concentrations of compatibilizing materials; e.g., a stable combination of aqueous DMDMH with parabens, at a weight ratio of 30:10, requires over 50% by weight of propylene glycol.

This requirement of a significant amount of compatibilizing material naturally dilutes the activity of the concentrate, limits the flexibility of paraben/substituted dimethyl hydantoin formulation for optimum performance, and creates formulating incompatibilities.

BRIEF DESCRIPTION OF THE INVENTION

In accordance with the invention, it has now been discovered that alkyl esters of p-hydroxybenzoic acid or combinations thereof may be advantageously formulated by dissolving these materials in molten lower alkyl-substituted dimethylhydantoins (DMH), specifically hydroxymethyl-substituted DMH, at the melt temperature of the latter. Such solutions cool to form a hard, waxy solid which can be converted to desirable forms by any of the well-known solids handling techniques, as, for example, by grinding into a powder.

By so dissolving the parabens in the substituted DMH, an intimate admixture of the materials is obtained which is clear in the molten state and has a melting point comparable to that of the substituted DMHs, though the melting point of the parabens may be considerably higher.

The compositions of the invention have numerous advantages over the prior art. For example, the combination of materials may be readily formed during the manufacturing stage, making unnecessary subsequent formulations of the two materials, provides complete flexibility of paraben levels to achieve the optimum broad spectrum properties, and gives a solid, stable formulation which is compatible with both oil- and water-based systems, which, surprisingly, does not suffer the incompatibilities of the prior art formulations which contain substantial levels of compatibilizing materials. In addition, the solid has an extremely high activity and low toxicity, and is active over a wide pH range at increased rates of solubility, as compared to the parabens per se. The molecular dispersion of the parabens in the blend provides a formulation of two materials that are well established as safe for use in the cosmetics and allied industries. The Council of Europe classifies aqueous solutions of the hydroxymethylated DMHs in the safest and the least toxic category; the parabens are widely permitted in foods in the U.K. and are given a GRAS ("generally recognized as safe") status by the Food & Drug Administration in the United States.

Accordingly, these solid formulations are clearly advantageous to the previously known liquid combinations.

DETAILED DESCRIPTION OF THE INVENTION

The lower alkyl-substituted dimethylhydantoins which may be used in the instant invention include compounds having the general formula:

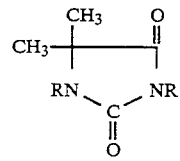

wherein at least one R, preferably both, are hydroxymethyl groups. Where only one R group is hydroxymethyl, the other is hydrogen, and the preferred compound is monomethylol dimethylhydantoin (MDMH).

As to the paraben component, these are lower alkyl esters containing from 1 to 6 carbon atoms in the alkyl group, most preferably the methyl, ethyl, propyl, and butyl esters. They may be used either alone or in combination. The preferred mixtures are of the methyl and propyl esters in a ratio of from 10:1 to 1:1, most desirably from 3:1 to 1:1.

To prepare the solid composition of the invention, any conventional procedure may be used to first liquefy the substituted dimethylhydantoin component and thereafter dissolve the paraben component. Generally in the case of DMDMH, the material is heated to the melting point and the mixtures of parabens are added to the melt. Dissolution occurs rapidly and, after stirring, the material may be cooled in any conventional manner and allowed to solidify. Thereafter, common grinding techniques may be used to form a free-flowing powder.

The solid materials may be incorporated into shampoos, creams, and lotions at any stage of their formulation, as is well known by those skilled in the art. Generally from 0.1 to 1.0 wt. % of the preservative is used, based on total composition, preferably from 0.1 to 0.8 wt. %.

Preferred compositions of the novel solid preservative of the invention contain about 65% of DMDMH and MDMH; from 34 to 35% of methyl and propyl parabens; and about 0.5% water. Most desirably, the DMDMH and MDMH to parabens weight ratio is at least 1:3, preferably 1:1 to 9:1. The following examples show the formation of a typical composition:

EXAMPLE 1

A mixture containing DMDMH, methyl paraben, and propyl paraben was prepared as follows: Fifteen grams DMDMH solid were placed in a 50 ml beaker immersed in a hot oil bath at 105° C. The DMDMH was allowed to melt and a mixture of 5.50 g methyl paraben and 1.50 g propyl paraben was added to the melt (the melting point of methyl paraben being approximately 125° C. and of propyl paraben approximately 95° C.). Dissolution occurred rapidly. The mix was allowed to stand for approximately 10 min. and was then discharged into an aluminum tray. The mixture solidified to a hard, waxy solid.

After grinding, the mixture has the appearance of a white powder and has a melting range of from 63° to 87° C. Products prepared in this manner typically contain 19% total formaldehyde, 30% methyl paraben, and 8% propyl paraben, and have a mild aromatic odor.

EXAMPLE 2

Solid DMDMH (31% total formaldehyde, 22.0 g) was added to a 100 ml round bottom flask. The flask was rotated while being heated in an oil bath at 105° C. until the DMDMH was completely melted (approximately 20 minutes). Methyl paraben (10.0 g) and propyl paraben (10.0 g) were then added and the flask once again rotated in the oil bath at 105° C. A clear melt resulted in about 10 minutes. The product was discharged onto a tray for solidification. Analysis of the solid product showed 16% total formaldehyde.

EXAMPLE 3

Thirty grams of solid DMDMH was melted as described in Example 2. To the clear melt was added 14.0 g of butyl paraben and the flask was rotated in the oil bath until the product was a clear melt once again. On such discharge, and solidification, the product was analyzed and found to contain 21% total formaldehyde.

Typical formulations using the solid admixture of the invention are set forth below:

| Creamy Aloe Shampoo | Percent |
| --- | --- |
| Aloe vera gel (Veragel Liquid 1:1) | 50.0 |
| Deionized water | 23.6 |
| Polyquaternium-7 (Merquat 550) | 3.0 |
| Sodium lauryl sulfate | 7.0 |
| Ammonium laureth sulfate | 5.0 |
| Sodium laureth sulfate | 5.0 |
| Lauramide DEA | 5.0 |
| Sodium chloride | 1.0 |
| Blend of Example 1 | 0.4 |
|  | 100.0 |

The components were formulated by adding all the ingredients and heating to 70° C. with stirring.

| Acid pH Conditioning Lotion | Percent |
| --- | --- |
| Di-2-ethyl hexyl adipate | 3.50 |
| Cetyl alcohol | 0.40 |
| Glycerol monostearate | 1.00 |
| Isocetyl stearate | 1.50 |
| Emulsifying wax, N.F. (Polawax) | 2.00 |
| PEG-40 stearate | 3.00 |
| Sentry grade propylene glycol | 4.00 |
| Polyquaternium 10 (Ucare Polymer JR-125) | 0.30 |
| Yeast | 0.10 |
| Blend of Example 1 | 0.50 |
| Water, fragrance | q.s. |
| Citric acid q.s. to pH | 5-5.5 |
|  | 100.0 |

I claim:

1. A solid preservative composition comprising a dispersion of an alkyl ester of p-hydroxybenzoic acid or mixtures of such esters in a hydroxymethyl-substituted dimethylhydantoin, wherein the aforesaid alkyl group has from 1 to 6 carbon atoms and the weight ratio of the hydantoin to the ester component is from 1:3 to 9:1.

2. The solid composition of claim 1 wherein the esters of the p-hydroxybenzoic acid are the methyl, propyl, and butyl esters.

3. The solid composition of claim 1 wherein the hydroxymethyl-substituted dimethylhydantoin is 1,3-bis(-hydroxymethyl)-5,5-dimethylhydantoin.

4. The solid composition of claim 2 wherein the ratio of the methyl to the propyl esters is from about 5:1 to 1:1.

5. A method of preparing a solid preservative composition which comprises: melting a hydroxymethyl-substituted dimethylhydantoin and adding thereto an alkyl ester of p-hydroxybenzoic acid or a mixture of such esters, dispersing said ester in said hydantoin component, and thereafter cooling said dispersion to form a solid homogeneous compound, wherein the aforesaid alkyl group has from 1 to 6 carbon atoms and the weight ratio of the hydantoin to the ester component is from 1:3 to 9:1.

6. The method of claim 5 wherein the solid compound is processed so as to form a comminuted mixture.

7. A formulated cosmetic containing effective amounts of a cosmetic and a preservative comprising from 0.1% to 0.8% of the composition of claim 1 therein.

8. A formulated shampoo containing effective amounts of a shampoo and a preservative comprising from 0.1% to 0.8% of the composition of claim 1 therein.

9. A formulated lotion containing effective amounts of a lotion and a preservative comprising from 0.1% to 0.8% of the composition of claim 1 therein.

* * * * *